(12) United States Patent
Mokrane

(10) Patent No.: US 9,101,490 B2
(45) Date of Patent: Aug. 11, 2015

(54) BODY FLUID MANAGEMENT SYSTEM

(76) Inventor: Mohamed Mokrane, Alger (DZ)

( * ) Notice: Subject to any disclaimer, the term of this patent is extended or adjusted under 35 U.S.C. 154(b) by 204 days.

(21) Appl. No.: 13/639,858

(22) PCT Filed: Apr. 6, 2011

(86) PCT No.: PCT/DZ2011/000002
§ 371 (c)(1),
(2), (4) Date: Oct. 6, 2012

(87) PCT Pub. No.: WO2011/124231
PCT Pub. Date: Oct. 13, 2011

(65) Prior Publication Data
US 2013/0046259 A1 Feb. 21, 2013

(30) Foreign Application Priority Data
Apr. 8, 2010 (DZ) .................................... 100198

(51) Int. Cl.
*A61M 1/00* (2006.01)
*A61F 5/451* (2006.01)
*A61F 5/442* (2006.01)

(52) U.S. Cl.
CPC ............... *A61F 5/451* (2013.01); *A61F 5/442* (2013.01)

(58) Field of Classification Search
CPC ................................. A61F 5/442; A61F 5/451
USPC .................................................. 604/349, 329
See application file for complete search history.

(56) References Cited

U.S. PATENT DOCUMENTS

| | | | | |
|---|---|---|---|---|
| 3,075,526 A * | 1/1963 | Morris | | 604/27 |
| 3,397,698 A * | 8/1968 | Hickey | | 604/353 |
| 3,601,125 A * | 8/1971 | Moss | | 604/347 |
| 3,602,923 A * | 9/1971 | Girala | | 4/144.1 |
| 4,820,291 A * | 4/1989 | Terauchi et al. | | 604/349 |
| 4,994,051 A * | 2/1991 | Walsh | | 604/349 |
| 5,002,541 A * | 3/1991 | Conkling et al. | | 604/319 |
| 5,097,540 A * | 3/1992 | Lovitt | | 4/443 |
| 5,334,174 A * | 8/1994 | Street | | 604/313 |
| 5,342,583 A * | 8/1994 | Son | | 422/107 |
| 5,797,890 A * | 8/1998 | Goulter et al. | | 604/351 |
| 5,864,895 A * | 2/1999 | Ota et al. | | 4/443 |
| 6,059,762 A * | 5/2000 | Boyer et al. | | 604/349 |
| 6,238,378 B1 * | 5/2001 | Perez | | 604/317 |
| 6,293,928 B1 * | 9/2001 | Fasani | | 604/279 |
| 6,651,267 B1 * | 11/2003 | Utz | | 4/449 |
| 6,918,896 B2 * | 7/2005 | McMurdo | | 604/279 |
| 7,875,010 B2 * | 1/2011 | Frazier et al. | | 604/329 |
| 8,187,238 B1 * | 5/2012 | Dupree | | 604/349 |
| 8,357,132 B1 * | 1/2013 | Lekweuwa | | 604/349 |
| 8,608,717 B2 * | 12/2013 | Tung | | 604/349 |
| 8,839,792 B2 * | 9/2014 | Brunner | | 128/844 |
| 2002/0177825 A1 * | 11/2002 | Scovel | | 604/353 |
| 2003/0181880 A1 * | 9/2003 | Schwartz | | 604/358 |
| 2003/0204176 A1 * | 10/2003 | Besoyan | | 604/353 |
| 2004/0143229 A1 * | 7/2004 | Easter | | 604/322 |
| 2007/0038193 A1 * | 2/2007 | Miskie | | 604/349 |
| 2007/0123833 A1 * | 5/2007 | Bruns | | 604/349 |
| 2007/0185465 A1 * | 8/2007 | Campbell et al. | | 604/347 |
| 2007/0260208 A1 * | 11/2007 | May | | 604/345 |
| 2009/0112171 A1 * | 4/2009 | Ng et al. | | 604/332 |

(Continued)

*Primary Examiner* — Susan Su
(74) *Attorney, Agent, or Firm* — Mark M. Friedman

(57) ABSTRACT

A system for managing and controlling bodily fluids such as urine and menstrual flow includes a garment with a latex envelope, for receiving the fluids from the male or female genitalia, and a system for disinfecting the male or female genitalia within the envelope.

6 Claims, 6 Drawing Sheets

(56) References Cited

U.S. PATENT DOCUMENTS

Figure 1:
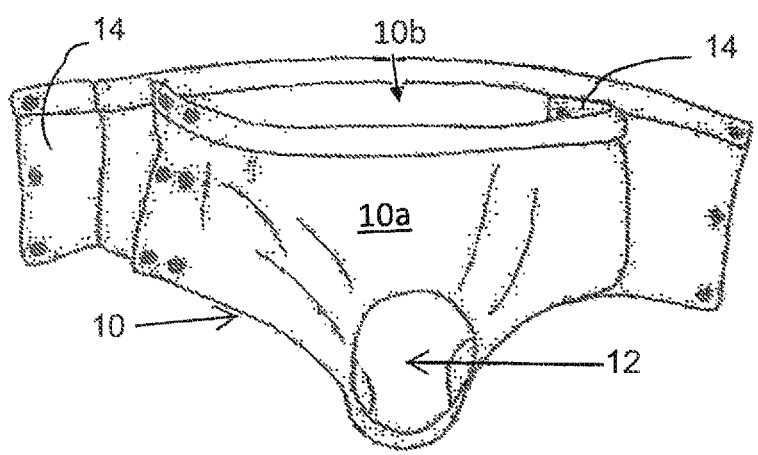

| | | |
|---|---|---|
| 2009/0270822 A1* | 10/2009 | Medeiros .................. 604/347 |
| 2010/0010459 A1* | 1/2010 | Piette et al. .................. 604/318 |
| 2011/0224636 A1* | 9/2011 | Keisic .................. 604/328 |
| 2012/0029452 A1* | 2/2012 | Rodsten .................. 604/353 |
| 2013/0237964 A1* | 9/2013 | Kicos .................. 604/544 |
| 2014/0350501 A1* | 11/2014 | Garcia Calero et al. ...... 604/353 |

* cited by examiner

BODY FLUID MANAGEMENT SYSTEM

TECHNICAL FIELD

Control of handicapping liquids consists of a device for the complete management of the flow of voluntary or involuntary urine, and the menstrual flow cycle for women in daily life, allowing for men and women to move unobtrusively.

BACKGROUND

For the management of incontinence of disposable absorbent plastic diapers, some of which for women, have a powder to freeze the urine and avoid overflow, there exists a system called PENI-FLOW™ connected to a collector, which is presently used.

SUMMARY OF THE INVENTION

The aim of the invention is to restore a normal quality of life for patients to manage incontinence, and for women to manage menstrual flow in order to allow them to move freely. As the invention allows Muslims a permanent hygiene, they achieve the accomplishment of ablution for their prayers. At the holy places of Islam at Mecca, during the days of Hajj, the invention allows its users to stabilize their movements, which will increase the area and therefore the number of pilgrims in Mina and Arafat Djebel, and avoid contacts reducing the contagious diseases epidemics to increase the safety of people and give them more rest.

The equipment of the present invention is autonomous, hermetic, lightweight, comfortable and discreet, and has a system of cleaning and sanitizing the penis and removal after urination, with an option of back pack tank with telescopic faucet, which can also perform the ritual of purification of body parts by water, in this case of occurrence of ablutions for Muslims.

DESCRIPTION OF THE DRAWING FIGURES AND THE INVENTION

Figure 6:
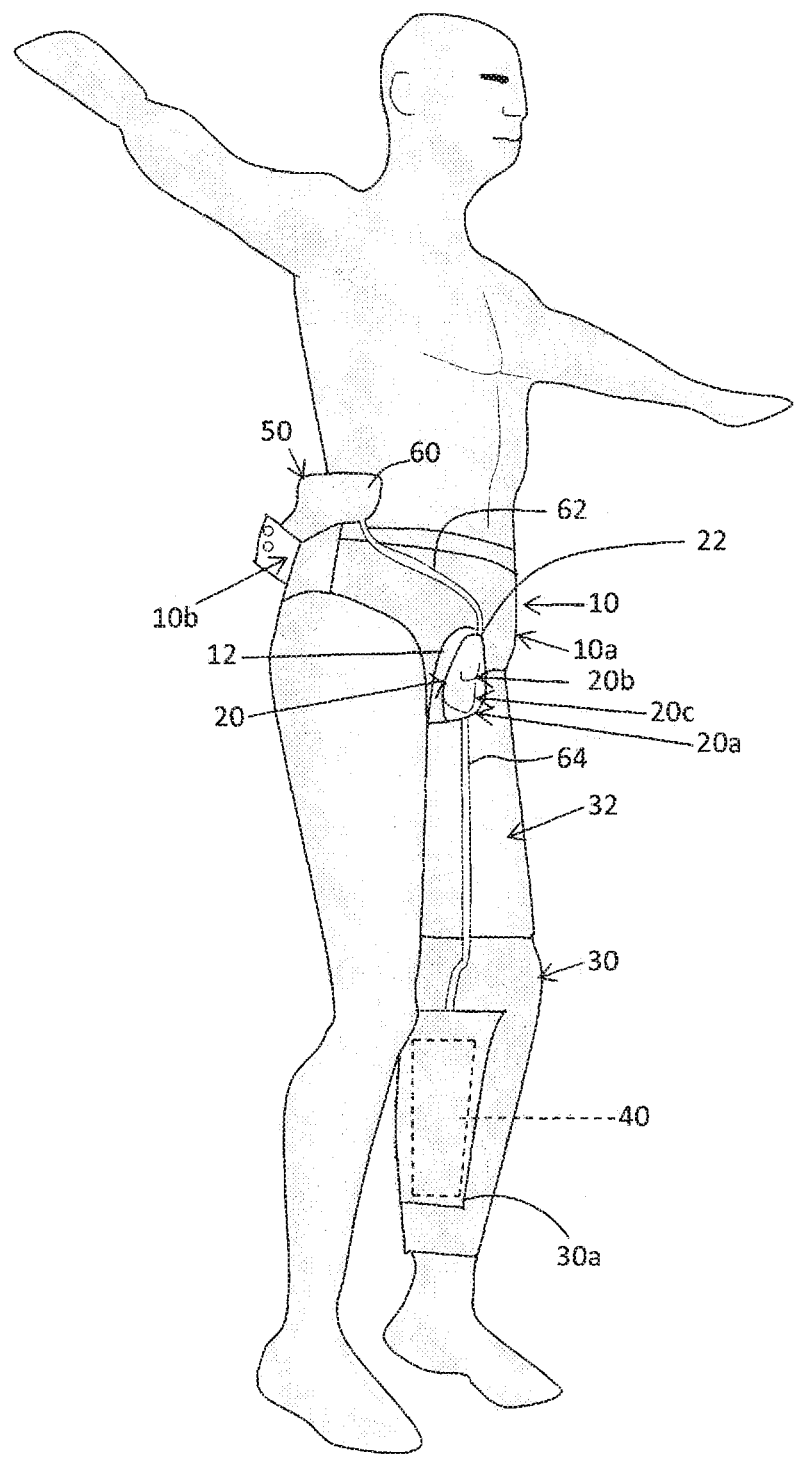

FIG. 1 shows a main slip. The main slip 10 consists of a slip or shorts 10 with an opening 12 for fixing the fringe of the envelope 20 (FIG. 2) to the skin, the envelope 20 serving as a urinal. Side openings 14, to defecate without the system being de-taped, keeping the front part 10a of the slip 10 which becomes independent of the rear part 10b. There is also an adjustable belt for the support of a wash pump 60 (FIG. 6).

Figure 2:
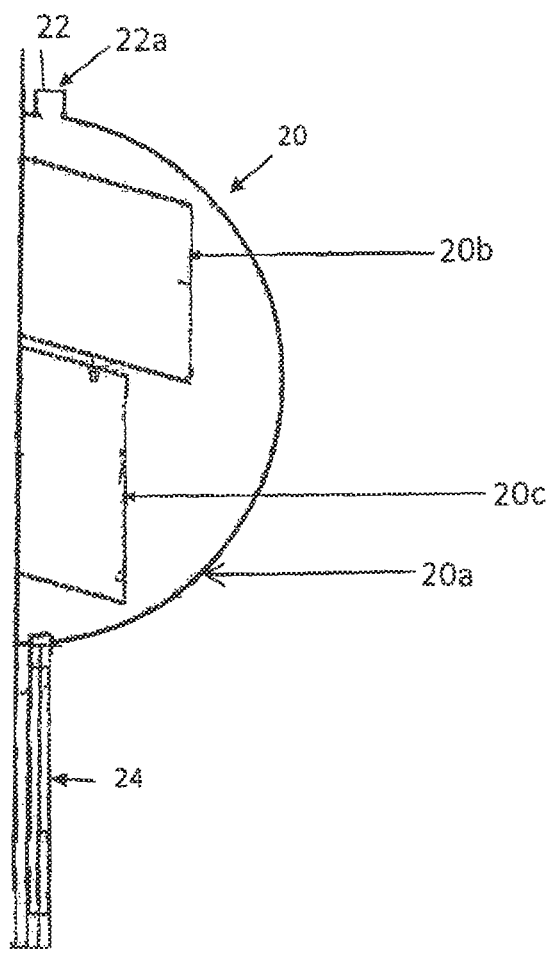

FIG. 2 shows a latex envelope 20. The envelope 20 is of a curved plane shaped like a half ellipsoid (having undergone a rotation about the major axis).

On this envelope 20 three parts 20a-20c are attached, which are:

a) The domed membrane 20a and flask that acts as a urinal in its outer part.

b) The sleeve 20b at the top (it is open) for receiving the penis.

c) The bottom pocket 20c to accommodate the scrotum:

The position of parts 20b and 20c will be the one for the use of the envelope 20 after loosening the mould (actually in the mould, the two parties will be reversed).

An opening 22 in a stub 22a at the top of the envelope 20 is reserved for the tube (line) 62 (FIG. 6) penetrating into the envelope 20. In fact the tube 62 enters the stub 22a secured to the envelope. The stub 22a is cylindrical and having is 5 mm in height and 5 mm in diameter.

The bottom tube (line) 64 coming out of the envelope 20 has an opening 24 having the shape of an inverted pyramid. This opening 24 acts as a funnel. This pyramid is formed of two sides of an equal and symmetrical trapezoid.

The elliptical flat surfaced part on the inner side of the envelope 20, matches the shape of the half ellipsoid. The extension of the surface part is a fringe, which extends an extra 3 cm for the attachment of the envelope 20 to the main slip 10 opening 12.

Figure 3:
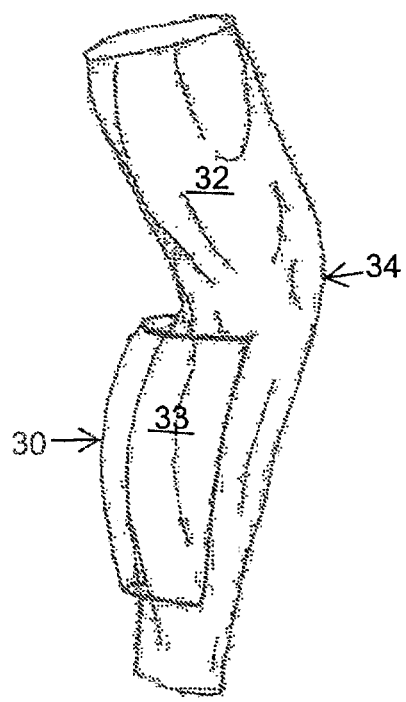

FIG. 3 shows a knee brace 30. The knee brace 30 is a holder (with a pocket 30a, as shown in FIG. 6) for a collector 40 (FIG. 4), and is attached to the leg 32, for example, the calf 33, proximate to the knee 34.

Figure 4:
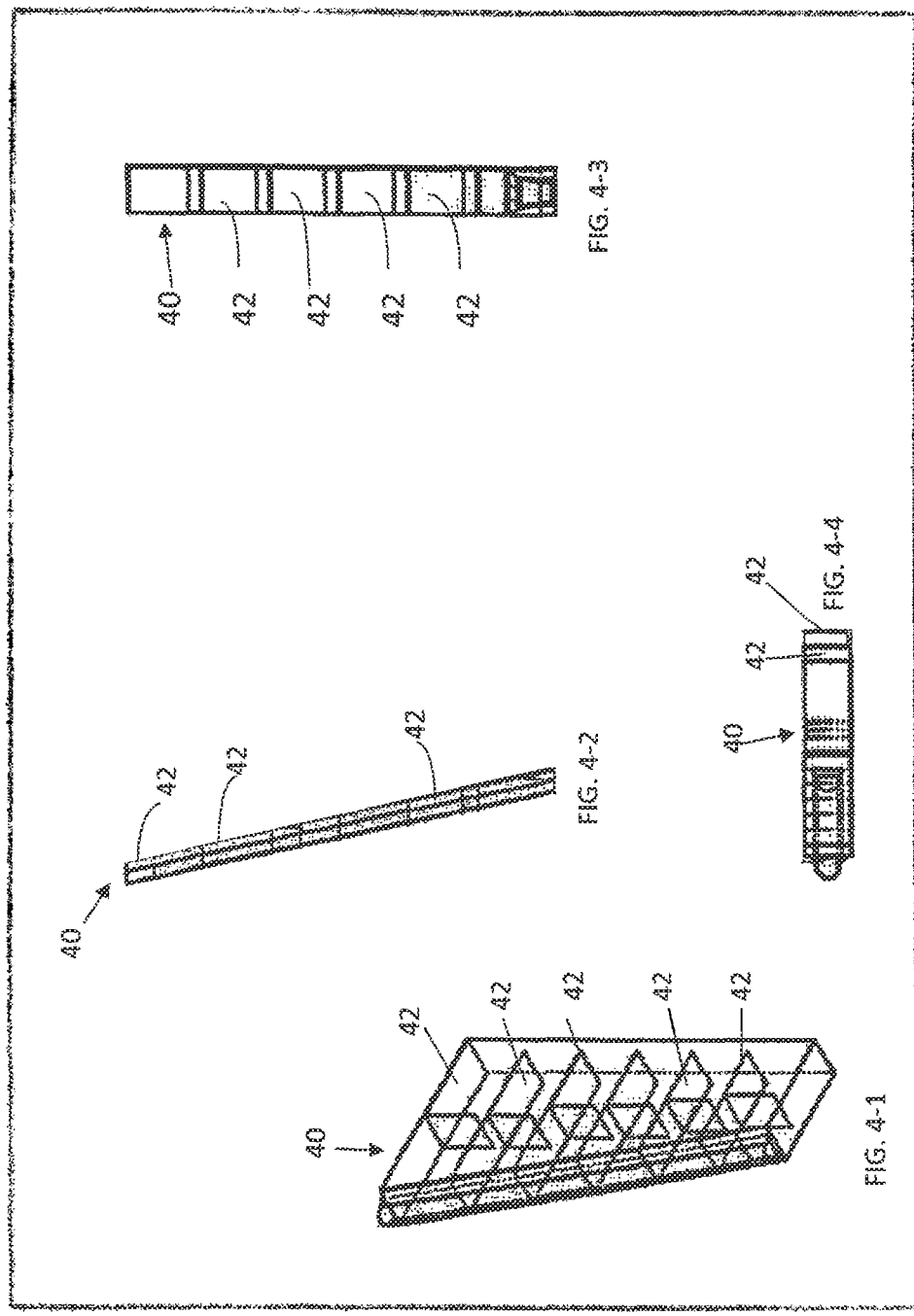

FIG. 4 shows a collector 40 in four views as FIGS. 4-1, 4-2, 4-3 and 4-4. The collector or collector packet 40 consists of honeycombs 42 in the form of bubbles or a hemisphere cut along a diameter, the bubbles which communicate with each other in order to avoid a bulging pocket effect upon the receipt and storage of liquids. The collector packet 40 is hermetic, flexible and/or elastic.

Figure 5:
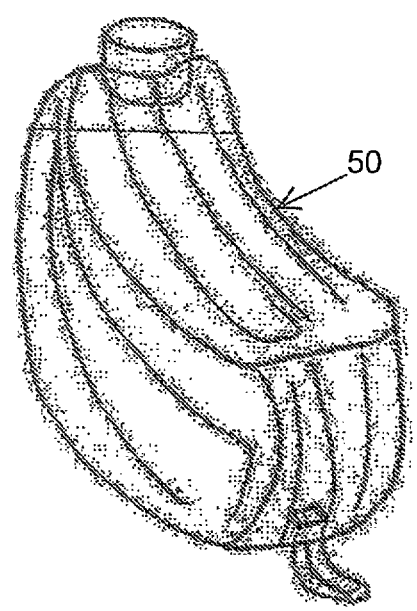

FIG. 5 shows a tank 50. A rectangular pump 60 connects to a container which is for carrying the washing and disinfection liquid for women to avoid microbial infection. The tank 50 is equipped with an exit hatch valve and a filling mouth and a tube 62 connecting the container of the tank 50 to the envelope 20 in its upper part. The pump 60 works by manual pressure and operates whenever needed.

FIG. 6 shows the present invention as worn by a male user.

Additional Components:

A container is located in the tank 50, which is positioned above the envelope 20 and placed so as to send the liquid with a strong flow of washing and disinfecting liquid through the tube 62.

The bottom tube 64 connecting the envelope 20 to the collector 40 is flat to accommodate high fluid flow. The bottom tube 64 extends from the funnel 24, which is the lower end of the envelope 20. The tube 62 connecting the pump 60 to the envelope 20 is conventionally rounded.

c) Valves:

There are four valves, the first two have different sizes have identical functions.

The collector valve comprises of a flap, which opens inwards, and serves to clamp the non return valve of the flat outlet nozzle coming from the envelope 20.

A pump valve is used to release the liquid for washing or disinfection by manual pressure (on the pump 60 and made of soft rubber). Its role is to stop the liquid or release it during the application of manual pressure.

A non-return valve is located at the end of the bottom tube 64, which connects the envelope 20 to the collector 40.

An air discharge valve functions to release air whilst preventing liquids to pass, facilitating the movement of liquid and evacuation to the collector 40. This valve will be located on the upper level of the envelope 20 about 10 mm cylindrical stump 22a. This valve is similar to those used in aquariums.

The adhesive to be used is a double-sided hypoallergenic adhesive. This adhesive serves to seal and close the urinal envelope 20 hermetically. The adhesive has a width of 15 mm for the man; it will take an elliptical shape so as to pass around the sleeve 20b for the penis and the scrotum pocket 20c. For the woman the side of the envelope 20 extends approximately 15 mm in an oval around the genital area.

An ablutions jacket is made of a single piece of latex material of a rectangular shape, where two pocket water tanks may be attached with two straps and a belt, with a 40 cm telescopic pipe, at its end a 7 cm valve rod with a half-circle, for performing closing and opening functions.

The invention is a system, shown being worn, for example, in FIG. 6, that can manage comprehensively, incontinence handicap, and menstrual flow of women, to provide the user the independence to urinate anywhere and at any time, even while moving.

The system has the following elements, including a slip 10, with a urinal envelope 20 with a sleeve for the penis 20b and scrotum 20c. A knee brace 30 with pockets 30a for the support of honeycomb collectors 40 to avoid a bulging effect. A manual pump 60 associated with fluid tank 50, for washing and disinfection of genitals, including post urination and menstruation. The collector 40 is partitioned into honeycombs 42, and has a large storage capacity and includes, pipes and valves.

There is also a back pack jacket (not shown) which has straps and a fastening belt (not shown). This jacket is designed to store water for the ablutions. It is equipped with a telescopic metal tube with half-moon designed faucet that can open and close in a flexible manner.

Methods for Manufacturing the Invention

Making the invention consists of moulding process of the following parts: the envelope 20 including the penis sleeve 20b and scrotum pocket 20c, in latex, by steeping technology. Moulding of hand pump 60 in soft rubber is performed by injection molding or press technology. Moulding of the honeycomb collector 40 is performed by injection molding or press technology in plastic. The knee brace 30 is made with in thin latex or elastic resistant fabrics. The bottom tube 64 is made of latex to accommodate high flows. The ablutions jacket is crafted in thin latex with straps and belts along with a telescopic tube.

Application

This invention relates to both sexes, adolescents and adults. As shown, for example, in FIG. 6, with reference also to FIGS. 1-5, use of the invention begins by placing the slip 10 as a panty and taping the edge of the envelope 20 around the penis and scrotum, with a double-sided anti-allergenic, medical adhesive, and then, adjusting the envelope 20 in the slip 10 according to the measurements by the side openings. The tank 50 is placed on the left hip in the hip belt and connect the tube 62. The knee brace 30 is attached above the knee 34 to the ankle. The honeycomb collector 40 is connected to the flow tube 62, this flow tube 62 provided with a non return valve, which is placed in a pocket 30a of the knee brace 30.

The user or patient wears the slip 10.

The user adjusts the device according to his size by the belts of the side openings. He places his penis in the penis sleeve 20b in urinal envelope 20 and places the scrotum into the pocket 20c. The envelope 20 is sealed to the skin by taping the envelope 20 to the skin with double-sided tape.

The male user He then sets the knee brace 30, fixes the pump 60, and attaches the collector 40 to the tip of the tube 62. When the user urinates, the flow is handled hermetically. First, the penis empties the urine into the urinal envelope 20, where it passes through the tube 64 along the inner thigh to flow into the collector 40. For women, fluid flow, urine or menstrual, is managed identically.

Then, the user or patient manually activates the pump 60, and pressure, acting on the opening valve, releases the pressurized liquid distributed by the container of the tank 50, for effective cleaning and disinfection of the genitals by water that contains an antiseptic. The disinfectant also cleans the tubes 62 and 64. The collector 40 is of a large capacity by design, and once filled, is detached from the tube 64. The valve automatically closes and the collector 40 is hermetically sealed to be thrown in the trash without risk of damage. The collector 40 is quickly replaced by a spare collector 40 and reinserted into the pocket of the knee brace 30.

The side openings of the slip 10 allow patients to defecate without de-taping the envelope 20 and adjusting the measurements.

The invention claimed is:

1. A body fluid management system comprising:
   an undergarment including an open area configured for supporting a fluid receiver;
   the fluid receiver being adapted to cover genitalia of a male user, the fluid receiver comprising a membrane, the membrane encloses an open sleeve for accommodating the penis and a pocket for receiving the scrotum;
   an inlet opening located on the membrane;
   an outlet opening located on the membrane;
   a wearable storage unit for holding washing fluid, the wearable storage unit configured to supply fluid to the fluid receiver via the inlet opening;
   a honeycomb collector in fluid communication with the fluid receiver via the outlet opening, the honeycomb collector configured to receive fluid from the fluid receiver;
   a brace for holding the honeycomb collector against a leg of the user; and,
   a pump in communication with the fluid receiver and the wearable storage unit, the pump, when activated, provides fluid from the wearable storage unit to the fluid receiver for cleaning the genitalia.

2. The body fluid management system of claim 1, wherein the undergarment includes a moveable portion to allow for defecation while the fluid receiver remains attached to the user.

3. The body fluid management system of claim 1, wherein the wearable storage unit is associated with a jacket.

4. The body fluid management system of claim 3, wherein the wearable storage unit includes disinfectant.

5. The body fluid management system of claim 1, additionally comprising a tube from the fluid receiver to the honeycomb collector and a one-way valve positioned along the tube.

6. The body fluid management system of claim 1, wherein the membrane is domed-shaped.

* * * * *